United States Patent [19]

Miyata et al.

[11] 4,314,380
[45] Feb. 9, 1982

[54] ARTIFICIAL BONE

[75] Inventors: Teruo Miyata; Taichiro Akiyama, both of Tokyo; Masayasu Furuse, Sagamihara, all of Japan

[73] Assignee: Koken Co., Ltd., Tokyo, Japan

[21] Appl. No.: 191,258

[22] Filed: Sep. 26, 1980

[51] Int. Cl.³ ............................ A61F 1/24; A61F 1/00
[52] U.S. Cl. ...................................... 3/1.9; 128/92 C; 128/92 G; 433/201
[58] Field of Search ...................... 3/1.9, 1; 128/92 C, 128/92 CA, 92 G, 1 R; 433/201

[56] References Cited

U.S. PATENT DOCUMENTS

| | | | |
|---|---|---|---|
| 2,968,593 | 1/1961 | Rapkin | 128/1 R X |
| 3,314,420 | 4/1967 | Smith et al. | 128/92 C |
| 3,443,261 | 5/1969 | Battista et al. | 3/1 |
| 3,628,248 | 12/1971 | Kroder et al. | 433/201 X |
| 3,767,437 | 10/1973 | Cruz | 3/1.9 X |
| 3,789,029 | 1/1974 | Hodosh | 128/92 C X |
| 3,790,507 | 2/1974 | Hodosh | 3/1.9 X |
| 3,892,648 | 7/1975 | Phillips et al. | 3/1.9 X |
| 3,929,971 | 12/1975 | Roy | 3/1.9 X |
| 4,222,128 | 9/1980 | Tomonaga et al. | 3/1.9 |
| 4,277,238 | 7/1981 | Katagiri | 3/1.9 X |

Primary Examiner—Ronald L. Frinks
Attorney, Agent, or Firm—Edward J. Mahler

[57] ABSTRACT

Artificial bone is prepared from animal bone treated for removal of organics, burned, baked and immersed in atelocollagen solution.

13 Claims, No Drawings

ARTIFICIAL BONE

This invention relates to an artificial bone which is prepared from animal bone by a process of removal of organic constituents, burning and baking, and thereafter immersing the baked bone in a solution of atelocollagen which becomes absorbed by the bone and coats the same. The artificial bone may be converted to desired shapes by known mechanical treatment. In a more specific embodiment of the invention, an organic polymer, e.g. acrylic, epoxy, urethane, etc. is impregnated into the bone before addition of atelocollagen.

PRIOR ART

The replacement of human bone in a living body with artificial or synthetic material has long been the subject of anatomical and chemical research. Numerous substitute materials have been proposed including plastics, ceramics, recrystallized glasses, metals and animal bone itself. Sterilized animal and human bone has not been very satisfactory due to immunological reactions prompting rejection of the implant by the human body. Numerous prior art patents, e.g. U.S. Pat. Nos. 3,929,971; 3,790,507; 3,789,029 and 3,628,248 disclose the existence of hydroxyapatite as a basic skeletal structure of bone. Japan Pat. No. 111,000 (1978) is concerned with the preparation of synthetic hydroxyapatite of particular particle size for use in making dental structures. Plastic bones containing acrylic polymers are disclosed in U.S. Pat. Nos. 3,790,507 and 3,789,029. M. M. Cruz, Jr. (U.S. Pat. No. 3,767,437) has prepared ivory or bone like structures from Battista's (U.S. Pat. No. 3,443,261) microcrystalline, partial salt of collagen by reacting such salt with a mesoamorphous salt of a polyvalent metal, e.g. calcium phosphate and drying the resulting gel product to form materials from sponge and cartilage densities up to hard ivories.

In the present invention the basic skeletal structure is porous animal bone residue (hydroxyapatite) obtained by treating animal bone for removal of organic constituents including chemical and thermal treatment, and thereafter immersing the baked bone in atelocollagen solution to reincorporate organic non-antigenic constituents.

ATELOCOLLAGEN

Collagen constitutes about 20 to 30 percent of the total body protein in vertebrates. It is a fibrous protein and functions primarily as a supporting tissue and scaffolding for other proteins and cells. It is present throughout the body but exists in high concentrations in skin, tendon and bone.

Collagen is recovered from these tissues by a variety of techniques the oldest known method being the boiling of the tissue in water which denatures some of the collagen and forms the well-known gelatin on cooling. For use as a biomaterial however, collagen must be recovered in native, undenatured form. i.e., with little or no destruction of the basic rigid triple helical structure; (tropocollagen).

The chemistry, molecular structure and biochemical properties of collagen have been well-established. A fairly recent review article (Annual Review of Biophysics and Bioengineering Vol. 3, p. 231-253, 1974) contains an excellent compilation of references on the subject.

The collagen solution used in this invention is enzyme-solubilized collagen which has preferably been treated for removal of fats and lipid bodies and which is free of telopeptides and relatively free of other contaminating antigenic proteins, mucopolysaccharides, etc. Enzyme-solubilized collagen is free of antigenic bodies.

The method of obtaining the collagen from the crude collagen source, e.g. skin, tendon, hide, etc., by enzyme extraction is as follows:

Cleaned, de-haired hide or skin is cut into pieces of workable size and slurried in water in the presence of a proteolytic enzyme (other than collagenase). Suitable enzymes are pepsin, trypsin, pronase, proctase, etc. The soluble extract is worked up as follows: The solution is brought to a pH of about 10.0 (when extracting for example with pepsin or proctase) to denature the remaining active enzyme, and then neutralized to a pH of about 6.7–7.0. Collagen precipitates at this pH leaving behind in solution (to be discarded) the digested telopeptides, and other contaminating proteins, e.g. albumin, globulin, and any saccharides, mucopolysaccharides, etc. Collagen from which such substances have been removed is known as "atelocollagen". The atelocollagen is usually further purified by repeated solubilization at pH 2–3, reprecipitation at pH 6–7 and recovered by filtration. The recovered collagen is then washed with ethanol to remove any lipid content and excess water in preparation for defatting. The collagen is defatted by treatment with 1:1 ethanol-ethyl ether mixture and recovered as a fibrous solid. It is then air-dried, and subsequently converted to gel by solubilization in citric acid acidified water at pH of about 3.0.

Atelocollagen concentrations ranging from 0.1% to 10 wt. % can be utilized for bone treatment but the preferable concentration is 0.5 to 5% with the balance being water.

Although the invention will be described as applicable to unmodified atelocollagen, it may also be applied to chemically modified atelocollagens in which the amino and/or carboxyl groups thereof have been subjected to esterification or acylation respectively, or both.

WORK-UP OF ANIMAL BONE

When an artificial bone is applied to a living body, it is most important that the artificial bone should show good affinity for the tissue of the living body. Organic materials included in such bone comprises cells, proteins, lipids, etc., which show antigen characteristics. Accordingly, if an animal bone is applied to the human body as it is, a rejection sympton arises. On the other hand, inorganic material of the bone comprises hydroxyapatite. Hydroxyapatite of animal bone is equivalent to that of human. Thus, the hydroxyapatite of animals is easily accepted by the human body and shows good tissue adaptation. When the hydroxyapatite is used as the principle bone ingredient, that is, inorganic constituent of an artificial bone, the applicability of such aritifical bone becomes acceptable and such applications are successful.

To obtain hydroxyapatite free of organic antigenic materials, the animal bone is subjected to chemical and thermal treatment steps as follows. The bone is scraped clean of any attached muscle or cartilage material and then immersed in 1 to 10% NaOH solution to which $H_2O_2$ has been added until the concentration of the whole solution becomes 1 to 5%. The animal bone is left in this state for 24 hours. The $H_2O_2$-NaOH solution is renewed daily and the operation is continued for about 1 to 3 weeks. A considerable amount of organic materials is removed to obtain a pure white animal bone. But the organic materials have not yet been completely removed. Therefore, the animal bone is burned at a temperature of the order of 600° to 1000° C. for 3 to 7 hours in order to completely remove the remaining organic material. Subsequently, the temperature is raised to 1000° to 1200° C. and the burned animal bone is baked for 2 to 5 hours at such temperature. In this manner, the pure inorganic constituent of animal bone is obtained which is constricted to some extent but keeps the original shape. The obtained bone is substantially hydroxyapatite.

The principle ingredient of organic materials included in bones is collagen. Collagen is important for the combining of inorganic materials with each other to impart proper strength to the bone. Therefore, collagen is impregnated into the above-mentioned baked bone in order that the bone has a composition closer to that of the living body and displays proper adaptability. Collagen used for such purpose, of course, must never show antigenic characteristics.

The atelocollagen used herein has biological properties as follows.

(1) It displays no antigen characteristics, no rejection symptom, and shows good adaptability with the living body.

(2) It shows good affinity with cells and works as a base for the production or proliferation of cells and further is effective to incorporate neighbouring tissue.

(3) It accelerates the restoration of injury in the combined tissue. When atelocollagen having such properties is impregnated into the bone of hydroxyapatite obtained by baking as described above, an artificial bone is obtained which shows good affinity with neighbouring bone tissue when embedded in a living body and is firmly bonded to the neighbouring tissue and bone cells. Furthermore, the impregnated atelocollagen is effective to improve the strength of artificial bone.

The impregnation of atelocollagen is effected as follows. The above-mentioned baked bone is immersed in 0.1 to 2% atelocollagen solution (buffer solution including 0.1 mol citric acid is used as a solvent) for one night under vacuum pressure and then air-dried. The immersed bone is washed several times with 50 to 90% alcohol solution in order to remove salts and then air-dried again. Subsequently, if necessary, cross-linking with ultraviolet rays or gamma-rays and/or a suitable tanning treatment with aldehyde etc. may be effected in order to improve the stability of the atelocollagen and/or the bond between the atelocollagen and hydroxyapatite.

For some applications, the strength of such artificial bone is improved when a polymerizable material such as a methacrylate is impregnated into the baked bone and polymerized before the above-mentioned atelocollagen treatment. For example, the baked bone is immersed in a solution which includes 95 to 97% methyl methacrylate, 4 to 2% acrylic acid and 0.1 to 1% benzoyl peroxide, and then the polymerization is effected in a sealed vessel at 90° C. for 10 to 60 minutes. Subsequently, the bone is immersed in the atelocollagen solution, air-dried, treated in order to remove salts, and again air-dried. By this manner, a stronger artificial bone is obtained.

The invention will be more fully understood from the following examples which are for purposes of illustrating the invention, and are not deemed to restrict the invention in any way thereto:

EXAMPLE 1

Preparation of atelocollagen

The atelocollagen used in this invention was prepared in accordance with the following procedure: Fresh calfskin (about 5 kg) was dehaired, cleaned by shaving and cut into small pieces. The skin was solubilized in twenty (20) liters of water (pH 3.0, HCl) by addition of 1 g of pepsin (approximate ratio of enzyme to collagen is 1/400) and kept at 20° C. for five days with intermittent stirring. The resulting viscous solubilized collagen was filtered through cheesecloth, then the filtrate is diluted to 0.5-1.0% collagen concentration and filtered through millipore filter of $0.65\mu$ pore size, its pH adjusted to 10 with NaOH and allowed to stand for 24 hours at 4° C. to inactivate the pepsin. The pH of collagen was then adjusted to 7 to 8 (HCl) and collagen precipitate was collected by centrifuging. Fatty constituents were then removed from the collagen. To one part of collected collagen was added two parts of fat solvent, e.g. ethanol ether mixture (1:1), and the mixture was homogenized in a Waring blender. Collagen was separated from solvent by squeezing in cheesecloth and homogenized again with the same volume of solvent. After being squeezed it was air-dried to remove solvent and redissolved in 0.1 M citric acid solution.

EXAMPLE 2

A rib of pig freed of lipids, fats and muscles, was immersed in 2% NaOH aqueous solution, to which $H_2O_2$ was added until the concentration of the whole solution becomes 2%. The rib was left in this condition for 24 hours. The $H_2O_2$ solution was renewed each day and this treatment was continued for 2 weeks so that a pure white bone was obtained. After the bone was washed with water and air-dried, it was burned at 700° C. for 5 hours and further baked at 1100° C. for 3 hours. The baked bone was immersed in 0.5% atelocollagen solution (atelocollagen was dissolved in 0.1 mole citric acid and the solution adjusted to pH 6.0 with NaOH) for one night under vacuum pressure in order to sufficiently impregnate the atelocollagen into the bone. After air-drying, it was washed twice with 50% aqueous alcohol solution to remove salts and then air-dried again.

EXAMPLE 3

A rib of pig which was cleaned of lipids, fats and muscles by similar manner to Example 2, was immersed in 5% $H_2O_2$ solution including 5% NaOH aqueous solution. The solution was renewed daily and the treatment was continued for 10 days. The resulting bone was washed with water and dried. Subsequently, it was burned at 800° C. for 4 hours and then baked at 1100° C. for 4 hours.

The baked bone was immersed in a solution which includes 97% methyl methacrylate, 2% acrylic acid and 1% benzoyl peroxide, for 1 hour and then enclosed in a glass tube and polymerized by heating.

The baked bone was then immersed in 1% atelocollagen solution (pH 6) under vacuum pressure for one night and air-dried. Subsequently, the baked bone was washed with 50% aqueous alcohol solution and again dried.

The resulting artificial bone was improved in strength in comparison with that obtained in the Example 2.

EXAMPLE 4

A bone prepared in accordance with Example 3 was impregnated with an epoxy resin rather than methacrylate. The epoxy used was Solution A 62 ml. of Epon-812 plus 100 ml. of dodecenyl succinic anhydride; and Solution B 100 ml. of Epon-812 plus 89 ml. of methyl nadic anhydride. Solutions A and B were mixed in a 1:1 ratio and the baked bone immersed therein. Air bubbles were removed by evacuation. After thorough impregnation, the bone was removed from the solution and heated at 60° C. for 24 hrs. After polymerization the bone was treated with atelocollagen in the manner of Example 2. Again, bone of improved strength was obtained.

EXAMPLE 5

A bone prepared in accordance with Example 3 was impregnated with polyurethane resin rather than methacrylate. Room temperature hardening type polyurethane ingredients (Kokusai Chemical Co.) were employed as follows: Reagent A—RU-13A polyhydroxy polyol; Reagent B—RU-13B methyl diisocyanate prepolymer. Six parts of Reagent A and 4 parts of Reagent B were mixed and the baked bone was immersed therein under vacuum. After impregnation the bone was removed from the reagent solution and kept at room temperature for 24 hrs. Another sample was polymerized by heating at 70°–80° C. for 3 hrs. The polyurethane reinforced bone was treated with atelocollagen as per Example 2 and again, increased strength was observed in the resulting bone.

Although pig bone was employed in the examples above, the bones of sheep, calf, cow, steer, lamb, etc. may be employed in the practice of this invention. In addition to rib bones other bone parts of the animal such as, humerus, femur, tibia, etc. may be employed. The resulting bone may be machined into various shapes for preparation of prosthetic devices. Plates, splints, pins, screws, caps, splines and other prosthetic parts may be fashioned from the finished bone.

In addition to the acrylic polymer resins, the epoxies, and polyurethanes, other organic polymers such as polyester resins and silicone resins may be used as strengthening agents for the artificial bone.

Having described the invention so that it may be practiced by those skilled in the art,

What is claimed is:

1. As an article of manufacture, an artificial bone comprising a core of porous, organic-free hydroxyapatite obtained from chemically-treated, burned, baked animal bone, said hydroxyapatite being impregnated and coated with atelocollagen.

2. An article of claim 1 in which the atelocollagen is cross-linked.

3. As an article of manufacture, an artificial bone comprising a core of porous, organic-free hydroxyapatite obtained from chemically-treated, burned, baked animal bone, said hydroxyapatite being impregnated and coated successively with an organic resinous polymer and with atelocollagen.

4. An article of claim 3 in which the polymer is an acrylate.

5. An article of claim 3 in which the polymer is an epoxy resin.

6. An article of claim 3 in which the polymer is a polyurethane.

7. An article of claim 3 in which the atelocollagen is cross-linked.

8. A method for the manufacture of an artificial bone which comprises:
   (a) soaking an animal bone in a caustic-$H_2O_2$ solution to remove the bulk of organic material therefrom,
   (b) burning the treated bone in air at a temperature in the range of 600°–1000° C. to remove remaining organic material therefrom,
   (c) baking the burned bone at a temperature in the range of 1000°–1200° C.,
   (d) immersing the baked bone in a solution of atelocollagen, and
   (e) removing from the solution, and drying, a bone impregnated and coated with atelocollagen.

9. A method of claim 8 in which an organic resinous polymer is incorporated into the baked bone prior to immersion in atelocollagen.

10. A method of claim 8 in which the atelocollagen is cross-linked after removal of the bone from the solution.

11. A method of claim 9 in which the organic resinous polymer is a polymethacrylate.

12. A method of claim 9 in which the organic resinous polymer is an epoxy resin.

13. A method of claim 9 in which the organic resinous polymer is a polyurethane.

* * * * *